United States Patent [19]

Favara et al.

[11] Patent Number: 4,576,746
[45] Date of Patent: Mar. 18, 1986

[54] NOVEL β-LACTAM ACETIC ACID DERIVATIVES

[75] Inventors: Duccio Favara, Como; Amedeo Omodei-Sale', Voghera; Pietro Consonni, Milan, all of Italy

[73] Assignee: Gruppo Lepetit, S.p.A., Italy

[21] Appl. No.: 354,572

[22] Filed: Mar. 4, 1982

[30] Foreign Application Priority Data

Mar. 12, 1981 [GB] United Kingdom ............... 8107865

[51] Int. Cl.$^4$ .................. C07D 205/08; C07D 487/04
[52] U.S. Cl. .......................... 260/239 A; 260/245.2 T
[58] Field of Search ................................... 260/239 A

[56] References Cited

U.S. PATENT DOCUMENTS

| | | | |
|---|---|---|---|
| 4,269,772 | 5/1981 | Melillo | 260/239 A |
| 4,282,148 | 8/1981 | Liu | 260/239 A |
| 4,287,123 | 9/1981 | Liu | 260/239 A |
| 4,290,947 | 9/1981 | Christensen | 260/239 A |
| 4,312,871 | 1/1982 | Christensen | 260/239 A |

FOREIGN PATENT DOCUMENTS 17992 10/1980 European Pat. Off. .

OTHER PUBLICATIONS

Kametani et al., J.C.S. Perkins I, 2228 (1981).
Favara et al., *Tet. Letters* 23, 3105 (1982).
Cama et al. J. Am. Chem. Soc., 100, 8006-7 (1978).
Kametani et al., J. Am. Chem. Soc., 102, 2060-5 (1980).
Ratcliffe et al., Tetrahedron Letters, 21, 31-4 (1980).
Cama et al., Tetrahedron Letters, 21, 2013-6 (1980).
Melillo et al., Tetrahedron Letters, 21, 2783-6 (1980).

*Primary Examiner*—Mark L. Berch
*Attorney, Agent, or Firm*—William J. Stein; Stephen L. Nesbitt

[57] ABSTRACT

New β-lactam acetic acid derivatives I

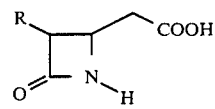

wherein R represents alkyl, alkyl substituted with amino, protected amino, mono- or di-alkylamino, hydroxy, protected hydroxy or alkoxy, and alkenyl, and their salts are useful as intermediates for preparing 1-azabicyclo [3.2.0]hept-2-ene antibiotics II

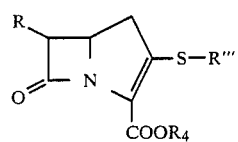

The process for preparing the β-lactam acetic acid derivatives I as well as the overall process which starting from the acids I leads to the antibiotics II are also claimed.

4 Claims, No Drawings

NOVEL β-LACTAM ACETIC ACID DERIVATIVES

The present invention relates to new β-lactam acetic acid derivatives useful as intermediates for 1-azabicyclo[3.2.0]hept-2-ene antibiotics, to the process for preparing them and to the overall process which starting from the new β-lactam acetic acid derivatives leads to 1-azabicyclo[3.2.0]hept-2-ene antibiotics.

A number of natural products containing the novel carbapen-2-em ring system have been isolated in the last few years from fermentation broths of Streptomyces strains. Representative of this family are: thienamycin, which was the first structurally-determined member,

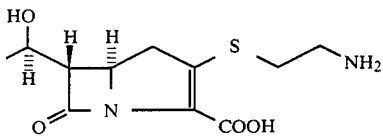

the antibiotic substance denominated PS-5 (R=COCH$_3$) and its corresponding N-desacetyl derivative NS-5 (R=H)

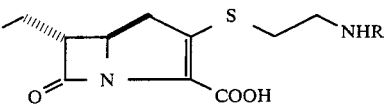

(see Belgian Pat. No. 865,578 and Japanese Patent application Publication No. 42536/80 respectively); the antibiotic substances PS-6 (R$_1$=CH$_3$, R$_2$=CH$_2$—CH$_2$—) and PS-7 (R$_1$=H, R$_2$=—CH=CH—)

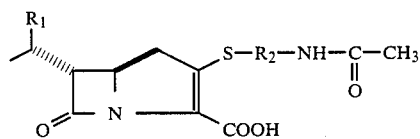

(see European patent application publication No. 1567), and the family of olivanic acids (R$_2$=—CH$_2$—CH$_2$— or —CH=CH—)

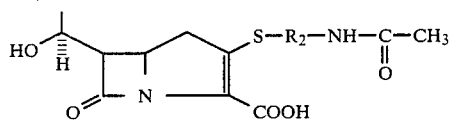

(see J. Antibiotics 32, 961–963, 1979).

The high antibacterial activity, the noteworthy breadth of the activity spectrum and the inhibitory activity against β-lactamases shared by these new substances, make them the most important compounds in this area from the biological point of view. This has stimulated investigations on total synthetic pathways to these compounds which have led to total syntheses of thienamycin and simpler carbapenem based analogs (see J.A.C.S. 100, 8006 (1978); J.A.C.S. 102, 2060–65 (1980); Tetr. Lett. 21, 31–34 (1980); Tetr. Lett 21, 2013–16 (1980); Tetr. Lett. 21, 2783–86 (1980), and European Patent Application Publication No. 17,992), and the synthesis of new classes of thienamycin analogs (see for instance European Patent Application Publication Nos. 828, 1,264, 1,265, 1,627, 1,628, 3,740, 5,349 and 8,888, Belgian Pat. Nos. 866,660 and 866,661, U.S. Pat. Nos. 4,150,145, 4,141,986.

The first object of the present invention is new β-lactam acetic acid derivatives of the following general formula

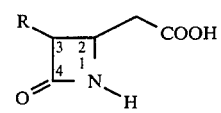

wherein R represents alkyl, alkyl substituted with amino, protected amino, mono- or di-alkylamino, hydroxy, protected hydroxy, or alkoxy, and alkenyl, and their salts which are useful as intermediates for preparing 1-azabicyclo[3.2.0]hept-2-ene antibiotics, such as those described in the literature referred to above, which bear a substituent R as above defined, at the 6-position of the carbapenem nucleus.

For the purpose of the present application, the term "alkyl", unless otherwise specified, identifies straight or branched alkyl radical of from 1 to 6 carbon atoms. With the terms "protected amino" and "protected hydroxy", it is intended to refer to an amino or hydroxy function respectively, protected by a group which is not affected by the reaction conditions, which will be described further on, employed for the synthesis of the acids I and for the use of the acids I in the process which lead to the 1-azabicyclo[3.2.0]hept-2-ene antibiotics. Examples of suitable protecting groups of the amino or hydroxy functions can be easily derived from the literature available in this field (see for instance "Protective Group in Organic Chemistry"—Edited by J. F. W. McOmie—Plenum Press—1973, pages 43 to 74 and 95 to 119) and typically include (C$_1$-C$_4$)alkanoyl optionally halo-substituted such as for instance acetyl, trifluoroacetyl, tert-butoxycarbonyl, and bromo-t-butoxycarbonyl, benzoyl, halo, nitro- or alkoxy substituted benzoyl, aralkoxycarbonyl such as for instance benzyloxycarbonyl and nitro-, halo- or alkoxy-substituted benzyloxycarbonyl, and the like.

The term "alkoxy" identifies straight or branched alkoxy radicals having from 1 to 6 carbon atoms, and the term "alkenyl" designates straight or branched alkenyl radicals containing from 3 to 6 carbon atoms and 1 or 2 double bonds.

The compounds of formula I above may exist in four different isomeric forms, two "trans" isomers, i.e. compounds I wherein the hydrogen atoms at position 2 and 3 have trans stereochemistry, and two "cis" isomers, i.e. compounds I wherein the hydrogen atoms at position 2 and 3 lie cis to each other. Formula I above therefore encompasses either mixtures of the optically active trans or cis isomers or the single optically active components. In most cases however the antibacterial activity of the final carbapenem antibiotics and their inhibitory activity against β-lactamases is tied to the trans configuration; therefore a preferred group of compounds of formula I includes those compounds in which the hydrogen atoms at positions 2 and 3 have trans stereochemistry.

The novel β-lactam acetic acid derivatives of the present invention are prepared through oxidation of the corresponding azetidinyl ethanol of formula II

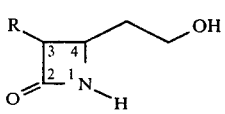

wherein R is as defined above.

For the oxidation of the ethanol (II) to the corresponding acid I, several different oxidizing agents may be employed such as for instance oxygen in the presence of a catalyst such as platinum adsorbed on carbon, the Jones reagent and permanganate; however the use of aqueous potassium permanganate buffered at a pH between 4 and 9, and preferably between 6.6 and 8.5, at room temperature, is preferred.

The alcohols (II) in their turn may conveniently be prepared according to either one of the two processes schematically represented in the following charts.

Chart I

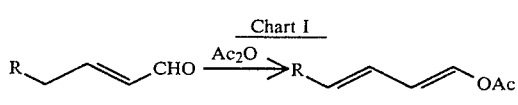

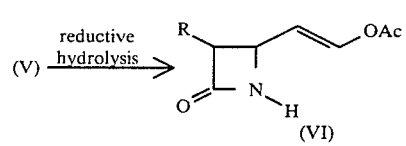

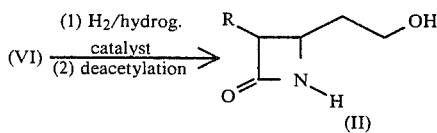

Chart II

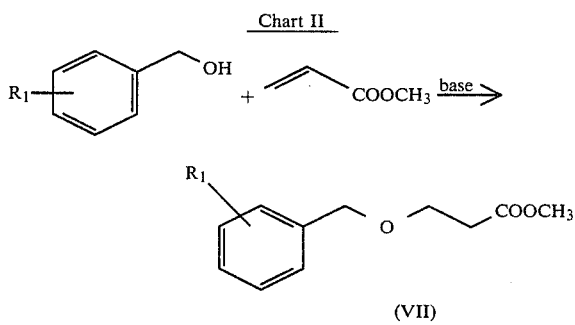

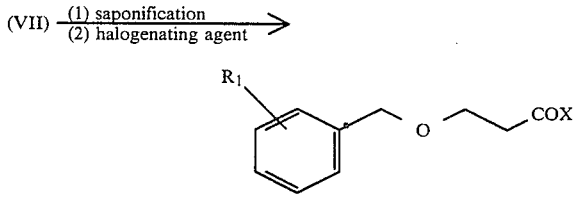

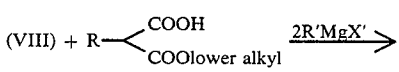

-continued
Chart II

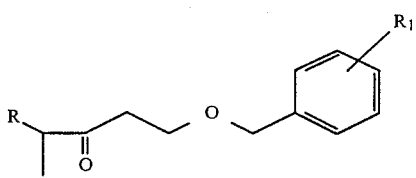

(IX) $\xrightarrow{\text{reductive amination}}$

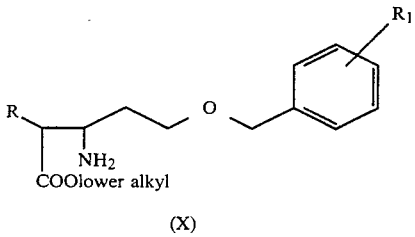

(X) $\xrightarrow{\text{R'MgX' (or LiR'')}}$

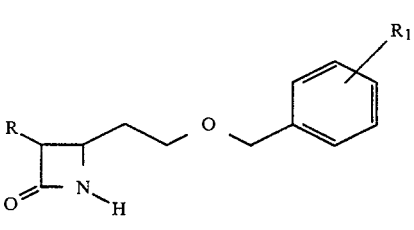

(XI) $\xrightarrow{\text{catalytic debenzylation}}$

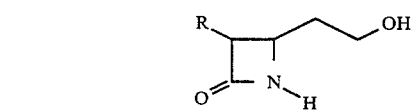

II

According to Chart I, the enol acetate of a trans-4-substituted-2-buten-1-al is reacted with chlorosulfonyl isocyanate to give the 2-azetidone (V) which is then submitted to reductive hydrolysis affording the 2-azetidinone (VI) in very high yields. The azetidinone (VI) is then submitted to hydrogenation followed by deacetylation yielding the desired azetidinyl ethanol (II). More particularly, the formation of the enol-acetate (IV) is achieved by reacting the aldehyde (III) with acetic anhydride in the presence of an organic or inorganic mild base such as a tertiary amine, or an alkali metal carbonate, and optionally, but not preferably, in the presence of an inert organic solvent. The reaction proceeds smoothly at room temperature, however sometimes it may be useful to heat the reaction mixture in order to speed up the reaction.

When acids I with trans stereochemistry at $C_2$ and $C_3$ are desired, the reaction between the aldehyde (III) and acetic anhydride is preferably carried out in the presence of a trialkyl amine, as the base, and in the presence of a catalytic amount of pyridine, 4-dimethylaminopyridine or N-methylimidazole. By following this procedure a cis/trans mixture of the enol-acetate (IV) is obtained wherein the percentage of the trans isomers is much higher than the expected 50%.

Alternatively, the enol-acetate (IV) may be prepared by reacting the trans-4-substituted-2-buten-1-al with isopropenyl acetate in the presence of catalytic amounts of p-toluensulfonic acid and cupric acetate.

The second step, i.e. the 2+2 cycloaddition of chlorosulfonyl isocyanate to the enol-acetate, is carried out in an inert organic solvent such as lower alkyl ethers, aliphatic and aromatic hydrocarbons, halogenated hydrocarbons, nitromethane, acetonitrile and the like, under inert atmosphere and keeping the temperature in the range of −20° C. to −5° C. This reaction may either be carried out as a batch or, more advantageously, as a continuous process. The organic solution containing the chlorosulfonyl derivative is submitted to reductive hydrolysis conditions by treatment with water buffered at a pH of about 6–8 containing a water soluble reducing agent such as sodium sulfite. The cycloaddition reaction followed by the reductive hydrolysis yields the β-lactam (VI) with a high ratio (more than 65%) of the trans isomer. This mixture may then be separated into the cis and trans isomers or it may be utilized as such for the subsequent steps.

The separation may be carried out by allowing the cis-isomer to crystallize out from the crude mixture and separating the crystalline material. The separation of the isomers may also be carried out by preparative HPLC on silica gel. The hydrogenation of (VI) may be carried out in the presence of a hydrogenation catalyst such as for instance Platinum or Palladium, preferably adsorbed on a carbon or asbestos inert carrier, or Nickel-Raney, at a temperature of from 20° to 60° C., under a pressure ranging from the normal pressure to about 20 atm. Preferably, the reduction is carried out at room temperature and under a pressure of about 3 atmospheres using a palladium on carbon catalyst. Solvents which may suitably be employed in this step are those commonly employed in hydrogenation reactions such as for instance ethyl acetate, dioxane, tetrahydrofuran, alcohols and the like. Finally, deacetylation to the alcohol II occurs in very high yields by treatment with methanol containing a base such as sodium methoxide or potassium carbonate or cyanide.

The six step synthesis reported in Chart II begins with the base-catalyzed addition of benzyl or substituted benzyl alcohol to methyl acrylate to give the 3-benzyloxy-propionic acid methyl ester (VII) wherein $R_1$ may represent hydrogen, lower alkyl, lower alkoxy, or nitro. The addition is carried out in the presence of an inert organic solvent which does not interfere with the reaction course, such as for instance benzene, toluene, xylene, and the like, using an alkali metal lower alkoxide or hydride or a tri-lower alkyl phosphine as the basic catalyst. Once the addition reaction is completed, saponification of the ester (VII) with aqueous sodium or potassium hydroxide may be carried out directly on the reaction mixture deriving from the addition reaction, without separation of the ester (VII) being required. 3-Benzyloxypropionic acid which forms is easily recovered from the reaction mixture by means of conventional procedures which involve acidification of the aqueous phase and extraction with a suitable organic solvent which is then boiled off. Reaction of the obtained 3-benzyloxypropionic acid with a halogenating agent, typically thionyl chloride, in the presence of a catalytic amount of dimethylformamide then affords the 3-benzyloxypropanoyl halide (VIII) wherein $R_1$ is as defined above and X is chlorine or bromine.

Condensation of the 3-benzyloxypropanoyl halide (VIII) with the magnesium salt of a malonic acid monolower alkyl ester derivative, obtained by treating a malonic acid monolower alkyl ester derivative

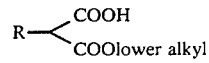

with a lower alkyl magnesium halide, yields the keto-ester (IX). The formation of the magnesium salt is achieved by contacting the malonic acid monolower alkyl ester derivative with the Grignard reagent R'MgX' wherein R' is a lower alkyl group and X' is chlorine, bromine or iodine in the presence of an inert organic solvent selected from those commonly employed in the Grignard reactions.

Once the salt is formed, 3-benzyloxypropanoyl halide is gradually added while keeping the temperature between about 10° C. and the room value.

By pouring the reaction mixture in aqueous mineral acids, extracting with an organic solvent immiscible with water, and evaporating off the extracting solvent, the keto-ester (IX) is recovered. If desired, the crude product (IX) thus obtained may be purified by means of the usual techniques or it can be used as such in the reductive amination step that leads to the amine derivative (X).

In this reductive amination, the carbonyl compound (IX) is treated with a large excess of ammonia, optionally in the form of its acetate, in the presence of a suitable reducing agent.

Sodium cyanoborohydride is a particularly preferred reducing agent, however other reducing agents can be used instead of sodium cyanoborohydride, among them hydrogen and a hydrogenation catalyst and sodium borohydride. The reaction which proceeds smoothly at room temperature and in alcoholic solvents, is preferably carried out at a pH of about 4.5–6.0 for instance by addition of glacial acetic acid.

Acidification of the reaction mixture with concentrated hydrochloric acid, filtration of the ammonium chloride which separates, and concentration of the filtrate to dryness affords a crude residue from which the compound (X) may be recovered by conventional purification procedures which are entirely familiar to any skilled chemist. Conversion of the amine derivative (X) to the β-lactam (XI) is achieved by treating the amine (X) with at least two equivalents, and preferably three equivalents, of a Grignard reagent, R'MgX', wherein R' is a lower alkyl group and X' is chlorine, bromine or iodine, or a lithium reagent R"-Li wherein R" stands for an alkyl, alkenyl or aryl group.

The reaction is carried out in an inert, organic solvent such as for instance ethyl ether, tetrahydrofuran, benzene, toluene, xylene and the like, and generally takes from 2 to 4 hours to be completed. The reactants are brought into contact at low temperature, from about −30° to about +5° C., and more preferably between −5° and +5° C., then the reaction proceeds at room temperature. Once the reaction is complete, diluted mineral acid is added at low temperature to give a final acid pH, preferably a final pH of about 3, and the β-lactam (XI) is extracted with a suitable organic solvent immiscible with water.

The compound (XI) which is recovered by evaporating the extracting solvent may then be purified by conventional procedures such as fractional distillation or chromatography or both.

Finally catalytic debenzylation of the β-lactam (XI), carried out according to the usual procedures known in chemistry, yields the alcohol II. Preferably, deprotection is achieved by using hydrogen and a hydrogenation catalyst, such as palladium adsorbed on carbon, in acetic acid and in the presence of a catalytic amount of a strong acid such as trifluoroacetic, sulfuric or hydrochloric acid.

When the trans-isomer of the acid I is desired, either the separation into cis- and trans-isomers is carried out at the β-lactam enol acetate (VI) stage, when the process described in Chart I is employed for preparing the alcohol II, or the cis/trans mixture of the acid I is separated into the couples of cis and trans isomers by crystallization from ethyl acetate.

Moreover, when a single cis or trans enantiomer of the acid I is desired, the cis or trans racemate of the acid I thus obtained, is then separated into the single optically active components by means of conventional procedures. These involve reaction with an optically active base, separation of the diastereoisomeric salts which form, by fractional crystallization or preparative HPLC, and separate restoration of the free acids.

Among the optically active bases which may suitably be employed in this separation, there are oxyphene, dehydroabiethylamine, brucine, rosine, cinconine, cinconidine, quinine, ephedrine and the like. Alternatively, "differential absorption" techniques, using absorption columns packed with chiral absorbents, may suitably be employed in this separation. When the trans-racemate or one of the trans-enantiomers of the acid I is desired, and the ratio of cis/trans isomers of the starting alcohols II is unfavourable, it may be convenient, before oxidizing the alcohol II to the acid I, to epimerize the mixture into the desired trans isomer through a sequence involving a protected intermediate of the formula

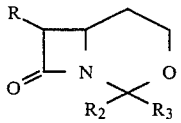
(XII)

wherein $R_2$ and $R_3$ independently, may represent a lower alkyl group or taken together an alkylene chain. The intermediate (XII) is formed through acid-catalyzed reaction of the alcohol II with a ketone, preferably acetone, diethylketone or cyclohexanone, or a ketal, typically 2,2-dimethoxypropane, in an inert aprotic organic solvent, then the epimerization of the protected intermediate is carried out using a strong base, such as for instance an alkali metal alkoxide or hydride, and preferably sodium or potassium t-butoxide or t-amylate, at a temperature generally ranging from about 0° C. to room temperature and preferably between 0° and 5° C.

The epimerization rapidly converts most of the cis isomer of the mixture into the trans form, then the alcohol II is restored by the addition of aqueous acetic acid.

When the process outlined in Chart II is employed for preparing the alcohol II, the epimerization may be carried out on the intermediate β-lactam (XI) with previous protection of the amino nitrogen atom through reaction with 2-methoxypropene in the presence of an acidic catalyst such as for instance borontrifluoride etherate or p-toluensulfonic acid. Also in this case the epimerization is carried out by using a strong base and deprotection is achieved by adding aqueous acetic acid.

As stated before the new β-lactam acetic acid derivatives of formula I are useful as intermediates for preparing 1-azabicyclo[3.2.0]hept-2-ene antibiotics. A further specific object of the present invention is the overall process which starting from the new β-lactam acetic acid derivatives of formula I leads to the desired antibiotics. This process, which is very simple, high yielding and adaptable to large scale operation is schematically represented in the following Chart:

Chart III

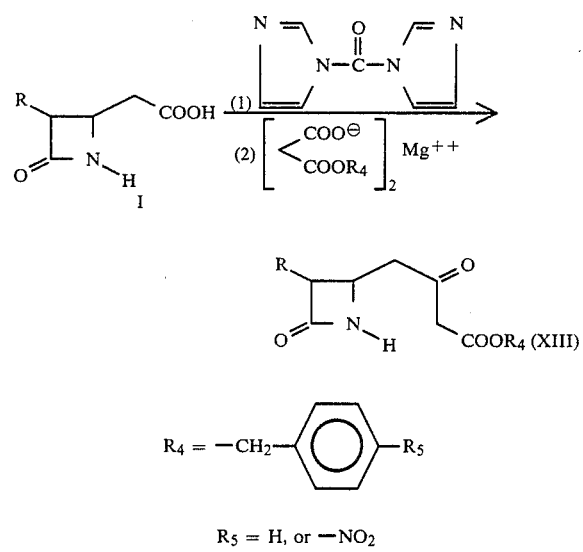

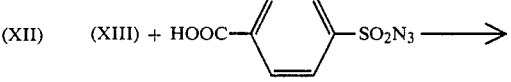

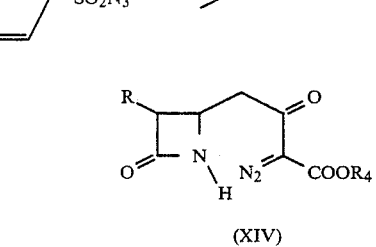

(XIII) + HOOC—⟨⟩—SO$_2$N$_3$ ⟶

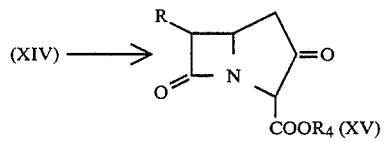

(XIV) ⟶ 

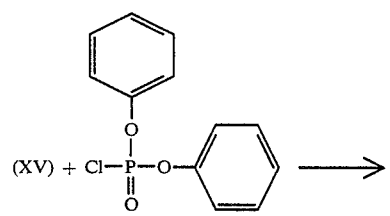

-continued
Chart III

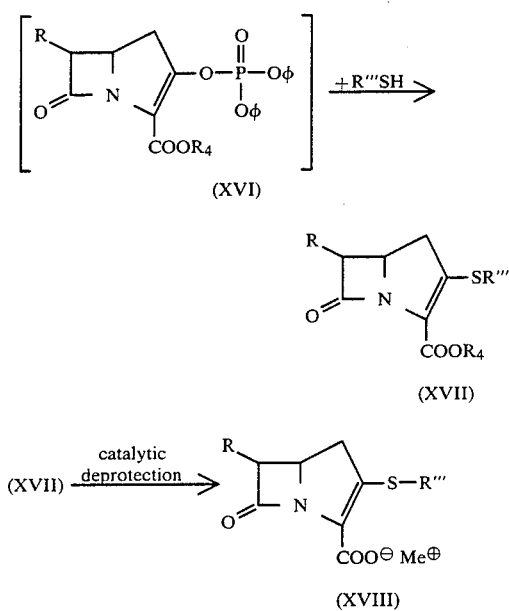

Me$^{\oplus}$ = alkali metal cation typically Na$^{\oplus}$ and K$^{\oplus}$

In the first step of the process described in Chart III, the side chain of the acid I is elongated by transforming it into the imidazolyl derivative and, without isolation, reacting it with the magnesium salt of monobenzyl or mono-p-nitrobenzyl malonate to yield the β-keto-ester (XIII). This product is subjected to a diazo-transfer reaction providing the α-diazo-β-keto ester (XIV). Rhodium (II) acetate-catalyzed decomposition of the diazo compound (XIV) affords the ring closure, through an NH insertion, to the bicyclic keto-ester (XV). The intermediate (XV) is converted to the enol phosphate (XVI), by reaction with diphenyl chlorophosphate to which a suitably selected nucleophile R'''SH, wherein R''' represents a variously substituted hydrocarbon group such as for instance a CH$_3$CO—NH—CH$_2$—CH$_2$— or CH$_3$CO—NH—CH=CH— group, is added affording the benzyl or p-nitrobenzyl ester(XVII). Finally catalytic deprotection of (XVII) affords the desired 1-azabicyclo[3.2.0]hept-2-ene. More particularly, the first step, i.e. the reaction of the acid I with carbonyldiimidazole followed by reaction of the obtained imidazolyl derivative with mono-benzyl or mono-p-nitrobenzyl malonate magnesium salt, easily proceeds in high yield at room temperature in a polar, aprotic, organic solvent such as tetrahydrofuran, dioxane, dimethyl sulfoxide and the like. The diazotransfer reaction which starting from the keto-ester (XIII) leads to the α-diazo-β-keto ester (XIV) is carried out in acetonitrile in the presence of an organic tertiary nitrogen base at a temperature comprised between 5° C. and room temperature. Decomposition of the ester (XIV) with a suitable catalyst typically selected from transition metal complexes, such as rhodium, copper, and platinum complexes, or Lewis acids such as for instance BF$_3$, affords the bicyclic keto ester (XV). When, according to a preferred embodiment, a catalytic amount of Rh$_2$(OAc)$_4$ is employed, by heating the catalyst first and then slowly adding the diazo (XIV) solution thereto, almost quantitative yields are obtained. The keto ester (XV) is then isolated by conventional procedures and converted to the enol phosphate (XVI) by reaction with diphenylchloro phosphate in acetonitrile, in the presence of a tertiary nitrogen base which acts as hydrogen chloride acceptor at low temperature and preferably at about 0° C.

The addition of the suitably selected nucleophile R'''SH to the reaction mixture containing the intermediate (XVI), carried out at low temperature, affords the benzyl or p-nitrobenzyl ester of the desired end 1-azabicyclo[3.2.0]hept-2-ene antibiotic (XVII). Finally, catalytic deprotection of the compound (XVII) is conveniently carried out at room temperature by means of hydrogen and a hydrogenation catalyst, preferably a palladium on carbon catalyst, using a mixture tetrahydrofuran/phosphate buffer pH 8 as the reaction solvent.

All the reaction steps outlined in Chart III proceed with retention of the configuration of the carbon atoms at positions 2 and 3 of the β-lactam acetic acid I; thus, when starting from the trans or cis racemates of the acid I, the corresponding trans or cis racemates of the final products (XVIII) are obtained when starting from a single trans or cis enantiomer I, one of the trans or cis enantiomers (XVIII) is obtained wherein the hydrogen atoms at the 5-, and 6-positions have the same absolute configuration of the starting acid I.

The following examples further illustrate the present invention but are not to be considered as a limitation of the scope thereof.

EXAMPLE 1

Trans-(±)-3-ethyl-4-oxo-2-azetidineacetic acid (I R=ethyl)

(a) Preparation of 1,3-hexadien-1-ol-acetate (Chart I–IV R=ethyl)

To a mixture of trans-2-hexenal (84.4 g; 0.86 mol) and acetic anhydride (102 g, 1 mol), 8 g (0.065 mol) of 4-dimethylaminopyridine and 105 g (1.04 mol) of triethylamine are added. The mixture is heated to 80° C. for two hours and then, after cooling at room temperature, 200 ml of chloroform is added. The organic layer is washed with two portions of 100 ml of ice-water and then with 30 ml of aqueous sodium bicarbonate. The chloroform layer is dried over MgSO$_4$. Evaporation of the solvent under vacuum yields a residue which is distilled at 80° C./60 mmHg. Yield 106 g. N.M.R. and I.R. Spectrum confirm the assigned structure. The product is a mixture of four isomers containing more than 65% of the Δ-3,4-(E)-isomers.

(b) Preparation of 4-[2-(acetyloxy)ethenyl]-3-ethyl-2-azetidinone (Chart I, VI R=ethyl)

1,3-Hexadien-1-ol acetate (105 g; 0.75 mol) is dissolved in 140 ml of ethyl ether under an atmosphere of argon at −15° C. To this solution, chlorosulfonyl isocyanate (126 g; 0.984 mol) in ethyl ether (126 ml) is added with stirring. Once the addition is complete, stirring at 0° C. is maintained for 3 hours and then the solution is added dropwise into a mixture of 225 g (1.75 mol) of sodium sulfite and 375 g (2.15 mol) of potassium hydrogen phosphate in 1100 ml of water and 900 ml of ethyl ether.

The mixture is stirred for 45 minutes on cooling with ice and solid bicarbonate is added to maintain the pH value at 6. The organic phase is separated and the aqueous layer is extracted with two 400-ml portions of ether. The combined organic layers are dried over magnesium sulfate and then evaporated to dryness under vacuum. The residue is suspended in 700 ml of petroleum ether and the mixture is stirred for 16 hours. After decantation the organic solvent is removed and the residue is dried under reduced pressure yielding 46 g of a product which boils at 120° C./0.1 mm Hg. Gas chromatographic assay shows that the product consists of a mixture of four isomers (trans-(Z), trans-(E), cis-(Z), cis-(E)). N.M.R. and I.R. spectra confirm the assigned structure.

The single components may be separated through preparative HPLC. The ratio of the desired trans isomers pair in the mixture is of about 80%.

(c) Preparation of 3-ethyl-4-[2-(hydroxy)ethyl]-2-azetidinone (Chart I, II R=ethyl)

The crude 4-[2-(acetyloxy)ethenyl)]-3-ethyl-2-azetidinone obtained according to step (b) above (46 g) is dissolved in 600 ml of ethyl acetate and, after addition of 1.6 g of 20% palladium on carbon catalyst, is hydrogenated at room temperature with a pressure of 3 atmospheres of hydrogen gas in a Parr autoclave. After three hours, the autoclave is discharged and the catalyst is filtered. Evaporation of the solvent yields 46.5 g of 4-[2-(acetyloxy)ethyl]-3-ethyl-2-azetidinone which boils at 110° C./0.03 mmHg. Gas chromatographic analysis of the product shows that the trans and cis isomers are in a 8:2 ratio. The isomers can be separated by preparative HPLC. The I.R. and N.M.R. data are in agreement with the assigned structure.

The crude 4-[2-(acetyloxy)ethyl]-3-ethyl-2-azetidinone is stirred with 9.7 g of potassium carbonate in 880 ml of absolute methanol at room temperature for 30 minutes. The mixture is neutralized with acetic acid and then evaporated to dryness at 50° C. under vacuum. The residue is suspended in a saturated aqueous solution of sodium chloride and the mixture is extracted with four 150-ml portions of ethyl acetate. The combined organic layers are dried over $MgSO_4$ and then evaporated to dryness yielding 34 g of 3-ethyl-4-[2-(hydroxy)ethyl]-2-azetidinone which contains 80% of the trans isomer (estimated by N.M.R.). The I.R. and N.M.R. data confirm the assigned structure.

(d) Preparation of trans-(±)-3-ethyl-4-oxo-2-azetidineacetic acid, I.

The crude 3-ethyl-4-[2-(hydroxy)ethyl]-2-azetidinone (34 g; 0.237 mol) obtained according to step (c) is added to 63 g (0.394 mol) of potassium permanganate and 79 g (0.59 mol) of potassium dihydrogen phosphate in 870 ml of water. The mixture is maintained under stirring at 15° C. for 22 hours, then 220 ml of a saturated solution of sodium metabisulfite are added thereto maintaining the value of the pH at about 3 by the gradual addition of 220 ml of 10% sulfuric acid. The mixture is stirred under cooling at 5° C. until a clear solution is obtained (about 30 minutes), then, after saturation with ammonium sulfate, it is extracted with four 250-ml portions of ethyl acetate. The organic extracts are pooled together and dried over $MgSO_4$. Concentration of the ethyl acetate solution to 100 ml and cooling overnight in a refrigerator gives a crystalline precipitate which is recovered by filtration. Yield 16.43 g of the product of the title. Concentration of the mother liquors yields 2.23 g of the product. Elemental analysis, I.R. and N.M.R. data are in agreement with the assigned structure.

The N.M.R. and I.R. spectra show the following characteristics:

N.M.R. spectrum, 60 MHz, δppm (DMSO d6): 0.93 (3H, t, $J_{CH_2-CH_3}=8$ Hz, CH$_3$), 1.63 (2H,dq,$J_{CH_2-H_3}=8$ Hz, C$\underline{H}_2$-CH$_3$), 2.60 (2H, d, $J_{CH_2-H_2}=8$ Hz, C$\underline{H}_2$—CO), 2.73 (1H, dt, $J_{H_3-H_4}=2.5$ Hz, H$_3$), 3.50 (1H, dt, H$_2$), 8.04 (1H,s, N-$\underline{H}$), 10.7–13.7 (1H, bb, COO$\underline{H}$).

I.R. spectrum (nujol): 330, 2580–2350, 1735, 1260, 975 cm$^{-1}$

EXAMPLE 2

Trans-(±)-3-ethyl-4-oxo-2-azetidinacetic acid (I R=ethyl)

(a) Preparation of 1,3-hexadien-1-ol acetate (Chart I–IV R=ethyl).

A mixture of trans-2-hexenal (5 g), isopropenyl acetate (10 ml), p-toluensulfonic acid (0.1 g) and copper acetate (0.025 g) is heated to 105° C. for 4–5 hours and as the acetone forms it is distilled. The reaction mixture is then cooled to room temperature, diluted with methylene chloride (30 ml) and washed with aqueous sodium bicarbonate. The methylene chloride is boiled, then the excess of isopropenyl acetate is removed by under vacuum distillation yielding a residue which is distilled at 79°–82° C./60 mmHg. Yield 4.5 g.

The next steps which lead to the compound of the title are carried out substantially as described in Example 1 b to d.

EXAMPLE 3

Trans-(±)-3-ethyl-4-oxo-2-azetidinacetic acid (I R=ethyl)

(a) Preparation of 3-benzyloxypropionic acid (Chart II, VII R$_1$=H)

Benzyl alcohol (20 ml) is added to 80% sodium hydride (0.9 g) placed in a dry 2-1 5-necked flask equipped with a mechanical stirrer, a condenser, a thermometer, a dropping funnel and an Argon inlet tube and the mixture is stirred slowly until the development of hydrogen ceases. Then, freshly distilled toluene (60 ml) is added, after which methyl acrylate (20 ml) is added dropwise into the obtained solution over a period of about 5 minutes, keeping the temperature at about 35°–37° C.

A mixture of benzyl alcohol (84 ml) and methyl acrylate (80.6 ml) is then added drop by drop to the stirred solution over a period of 20–30 minutes, and stirring is continued for additional 20 minutes. Once the reaction, which is monitored by gas chromatography, is completed, 4N KOH (500 ml) is added and the mixture is stirred at room temperature for 2 hours. Then, 8% HCl (420 ml) is added keeping the temperature at about 20°–25° C. and the mixture is extracted with methylene chloride (200 ml plus four 50-ml portions). The mother liquors are acidified with 37% HCl (102 ml) to reach a pH of about 2.5 and extracted again with toluene (200 ml plus three 100 ml portions) The toluene extracts are combined, dried over $Na_2SO_4$, and concentrated to dryness yielding an oily residue of 3-benzyloxypropionic acid (100 g) which is employed as such in the next step.

(b) Preparation of 3-benzyloxypropionyl chloride (VIII R$_1$=H, X=Cl)

Thionyl chloride (60 ml) is added dropwise into a 500 ml four-necked flask fitted with a mechanical stirrer, a thermometer, a condenser and a dropping funnel, charged with 3-benzyloxypropionic acid (100 g).

Dimethylformamide (two drops) is then added while the temperature is kept at about 20° C. by means of a warm water bath. After stirring at room temperature for 2 hours the excess of thionyl chloride is removed by vacuum distillation and the residue is taken up twice with methylene chloride (two 100 ml portions). By evaporating the methylene chloride under reduced pressure 3-benzyloxypropionyl chloride (108.8 g) is obtained.

(c) Preparation of 5-benzyloxy-3-oxo-2-ethyl-pentanoic acid ethyl ester (IX R=ethyl $R_1$=H)

Ethyl bromide (5 ml) is added dropwise into a 2 l five-necked flask equipped with a mechanical stirrer, a condenser, a dropping funnel, a thermometer and an Argon inlet tube charged with magnesium turnings (26.6 g), anhydrous tetrahydrofuran (100 ml) and iodine (a few crystals). After 1 or 2 minutes, once the reaction begins, the mixture is stirred and diluted with anhydrous tetrahydrofuran (510 ml). Ethyl bromide (86.6 ml) is gradually added, over a period of 45 minutes keeping the temperature at about 30°–35° C. When the ethyl bromide has been added stirring is continued for an additional 30 minutes and the mixture is cooled to about −10° C. Then a solution of ethyl malonic acid monoethyl ester (87.7 g) in anhydrous tetrahydrofuran (80 ml) is slowly added dropwise (60 minutes) into the above mixture. When the addition is complete, the mixture is stirred for one hour at room temperature and for an additional hour at about 75° C. The mixture is then cooled to 15° C. and a solution of 3-benzyloxypropionyl chloride (108.8 g) in anydrous tetrahydrofuran (50 ml) is added drop by drop over a period of 15 minutes. After stirring at room temperature for two hours, the reaction mixture is allowed to stand at room temperature overnight and gradually poured into a 3-l beaker, equipped with a mechanical stirrer and a thermometer, containing 8% HCl (295 ml) and toluene (295 ml), keeping the temperature at about 10°–15° C. After stirring for a few minutes, the aqueous phase is separated and extracted with toluene (three 150-ml portions). The toluene extracts are combined, washed with a 15% phosphate buffer pH 6.5 (two 250-ml portions), dried over $Na_2SO_4$ and concentrated to dryness yielding 5-benzyloxy-3-oxo-2-ethyl-pentanoic acid ethyl ester (146.8 g). The ethylmalonic acid monoethyl ester used in this step has been prepared as follows:

A solution of ethylmalonic acid diethyl ester (123.6 g) in 95% ethanol (650 ml) is placed in a 1-l four-necked flask fitted with a mechanical stirrer, a condenser, a thermometer and a dropping funnel, and cooled to about 10° C. A solution of NaOH (26.8 g) in water (33 ml) is added dropwise into the above solution over a period of 15 minutes. The mixture is allowed to go to room temperature and stirring is continued for about 1 hour until a neutral pH is reached. By evaporating the solvent under vacuum and heating to about 30°–35° C., a residue is obtained which is taken up with water (400 ml) and extracted with toluene (two 130-ml portions). The toluene extracts are washed with water and the aqueous phase plus the aqueous wash are brought to pH 2 by the addition of 37% HCl (50 ml) and extracted with methylenechloride (four 125-ml portions). The methylene chloride extracts are combined, dried over $Na_2SO_4$ and concentrated to dryness yielding ethylmalonic acid monoethyl ester (87.7 g) as a thick oil.

(d) Preparation of 3-amino-5-benzyloxy-2-ethyl-pentanoic acid ethyl ester (X R=ethyl $R_1$=H)

The compound 5-benzyloxy-3-oxo-2-ethyl-pentanoic acid ethyl ester (146.8 g), methanol (1580 ml) and ammonium acetate (406.2 g) are charged in a 6-l five-necked flask equipped with a mechanical stirrer, a condenser, a thermometer, an Argon inlet tube, and a dropping funnel, and the mixture is stirred until a complete solution is obtained. Then sodium cyanoborohydride (16.6 g) is added thereto and, after 5 minutes, glacial acetic acid (330 ml). Stirring is continued for 40 hours at room temperature, then the temperature is lowered to −5° C. and a strong Argon stream is passed through the reaction mixture. 37% HCl (540 ml) is added drop by drop over a period of 20 minutes to lower the pH to about 2.5 and the bubbling Argon stream is continued while the temperature is allowed to rise to room temperature. Ammonium chloride which separates is filtered under vacuum and washed with methanol. The filtrate plus the methanol wash are concentrated to dryness under reduced pressure by heating to 40°–45° C. The residue is taken up with 5% HCl (400 ml) and toluene (900 ml) and the toluene layer is separated and extracted with 5% HCl (three 300 ml portions). The acidic extracts are combined, cooled to about −5° C. and brought to pH 8 by the addition of 50% NaOH (550 ml). The mixture is extracted with methylene chloride (four 300-ml portions) which is then dried over $Na_2SO_4$ and concentrated to dryness under reduced pressure yielding 3-amino-5-benzyloxy-2-ethyl-pentanoic acid ethyl ester (99.1 g) which may be used as such in the next step.

(e) Preparation of 4-(2-benzyloxyethyl)-3-ethyl-azetidin-2-one (XI R=ethyl $R_1$=H)

A solution of ethylmagnesium bromide prepared by following the procedure described in step (c) above but starting from 25.9 g of magnesium turnings, 440 ml of anhydrous tetrahydrofuran, 84.4 ml of ethyl bromide, and 0.1 g of iodine, is placed in a 2-l five-necked flask fitted with a mechanical stirrer, a condenser, a dropping funnel, a thermometer and an Argon inlet tube. A solution of 3-amino-5-benzyloxy-2-ethyl-pentanoic acid ethyl ester (99.1 g) in anhydrous tetrahydrofuran (220 ml) is added dropwise into the above solution cooled to −5° C./0° C. The reaction mixture is then allowed to rise to room temperature and stirring is continued for two additional hours, after which the reaction mixture is cooled again to −5° C. 8% HCl (480 ml) is added dropwise into the mixture to bring the pH of the reaction mixture to about 3, and then toluene (300 ml) is added. The aqueous phase is separated and extracted with toluene (two 200-ml portions) and the organic extracts are combined, washed with an aqueous solution saturated with NaCl, dried over $Na_2SO_4$ and evaporated to dryness under vacuum to yield a thick, dark oily residue (86.2 g). This residue is dissolved in toluene (50 ml) and the resulting solution is applied to a silicagel column prepared in toluene. The column is developed using toluene (500 ml), then toluene:ethyl acetate 75:25 (500 ml), toluene:ethyl acetate 50:50 (600 ml) and finally ethyl acetate (700 ml) and collecting 150-ml fractions. Elution of the column is monitored by thin-layer chromatography. Fractions 5 to 15 are combined and evaporated to dryness under vacuum yielding 4-(2-benzyloxyethyl)-3-ethyl-azetidin-2-one (58.5 g) as a 6:4 cis/trans mixture.

(f) Preparation of 3-ethyl-4-(2-hydroxyethyl)-azetidin-2-one (II R=ethyl)

A 1-l flask connected to a hydrogenation apparatus and placed on on air driven magnetic stirrer is charged with 4-(2-benzyloxyethyl)-3-ethyl-azetidin-2-one (19.5 g), glacial acetic acid (200 ml) trifluoroacetic acid (9.47 ml) and 10% Palladium on carbon (2.9 g). The mixture is hydrogenated at room temperature and pressure for about 3 hours, then the catalyst is removed by filtration under vacuum, washing with acetic acid. The solvent is evaporated under reduced pressure by heating to 40°–50° C. and the obtained residue is dissolved in methanol (150 ml). Anhydrous potassium carbonate (17.27 g) is added to the resulting solution and the obtained mixture is stirred for 30 minutes. The inorganic salts are removed by filtration and the filtrate is brought to pH 6 by the addition of dilute acetic acid. The residue which is obtained by evaporating the solvent is taken up with water (100 ml) and extracted with toluene (three 50-ml portions). The toluene extracts are washed with a small amount of water and then discarded while the mother liquors plus the aqueous washes are combined, saturated with $(NH_4)_2SO_4$ (100 g) and extracted with ethyl acetate (five 50-ml portions). The organic extracts are dried over $Na_2SO_4$ and evaporated to dryness under vacuum yielding 9.7 g of 3-ethyl-4-(2-hydroxyethyl)-azetidin-2-one as a 6:4 cis/trans mixture.

(g) Epimerization of the 6:4 cis/trans mixture of 3-ethyl-4-(2-hydroxyethyl)-azetidin-2-one.

The cis/trans mixture obtained in step (f) above (9.7 g), toluene (60 ml), 2,2-dimethoxypropane (10.2 ml) and p-toluenesulfonic acid (0.6 g) are placed in a 250-ml three-necked flask equipped with a magnetic stirrer, a thermometer, a Dean-Stark apparatus and an Argon inlet tube. After stirring at room temperature for 18 hours, the mixture is heated to 130°–140° C. and 36 ml of solvent are distilled which are replaced by 24 ml of freshly distilled toluene. The reaction mixture is then cooled to 0° C. and a 1.5 N solution of sodium tert-amylate in xylene (36 ml) is added drop by drop keeping the temperature in the range 0°–5° C. Stirring is then continued at room temperature for two hours after which a solution of $NaH_2PO_4 \cdot H_2O$ (19.4 g) in water (100 ml) is added. The aqueous phase is separated and extracted with ethyl acetate (four 50-ml portions). The organic extracts are combined, washed with an aqueous solution saturated with NaCl (two 25-ml portions), dried over $Na_2SO_4$ and concentrated to dryness. The obtained residue is dissolved in 10% acetic acid (100 ml) and stirred at 70° C. for 3 hours. After cooling to room temperature the mixture is extracted with methylene chloride (three 30-ml portions). The organic extracts are washed with water and then discarded, while the mother liquors and the aqueous washes are combined, brought to pH 5.5–6 by the addition of 10% NaOH (50 ml), and saturated with $(NH_4)_2SO_4$ (150 g). By extracting with ethyl acetate (five 30-ml portions), drying the organic extracts over $Na_2SO_4$, and evaporating the solvent under vacuum a 1:9 cis/trans mixture of 3-ethyl-4-(2-hydroxyethyl)-azetidin-2-one (6.41 g) is obtained.

(h) Preparation of trans-(±)-3-ethyl-4-oxo-2-azetidinacetic acid (I R=ethyl)

A mixture of the crude 3-ethyl-4-[2(hydroxy)ethyl]-2-azetidinone (6.41 g) obtained according to step (g) above, sodium phosphate bibasic (5.5 g) and sodium phosphate monobasic (3.4 g) in water (65 ml) is stirred for 20 minutes at room temperature. The pH of the solution is brought to 6.6 by the gradual addition of 10% sodium hydroxide (4.6 ml). The temperature is lowered to 15° C. and potassium permanganate (9.92 g) is added. The reaction mixture is stirred at 15°–20° C. for 24 hours maintaining the pH in the range of 6.6–8.5 by the gradual addition of 10% sulfuric acid (4.6 ml). The mixture is cooled to 5° C. and the excess of potassium permanganate is reduced by adding dropwise a 3.3M sodium meta-bisulfite solution (about 1.5 ml). After removing manganese dioxide by vacuum filtration on Celite, the clear aqueous solution is saturated with ammonium sulfate, brought to pH 3.5 with 10% sulfuric acid, and extracted with ethyl acetate (90 ml followed by four 40-ml portions). The combined extracts are dried over magnesium sulfate and concentrated under reduced pressure at 35° C. to a small volume. Crystallization is allowed to proceed at room temperature and then for two days at 0° C. The precipitate is removed by filtration and dried under vacuum. The yield in crystalline trans-(±)-3-ethyl-4-oxo-2-azetidinacetic acid is 3.2 g (48%).

Elemental analysis, I.R., and N.M.R. data are in agreement with the assigned structure.

EXAMPLE 4

Trans-(±)-3-ethyl-4-oxo-2-azetidineacetic acid (I R=$CH_3CH_2$—)

The compound of the title may also be prepared by following the procedures described in steps (a) to (e) of example 3 submitting the obtained 6:4 cis/trans mixture of 4-(2-benzyloxyethyl)-3-ethyl-azetidin-2-one to epimerization, and then proceeding as described in steps (f) and (h) of the above example. More particularly, the epimerization of 4-(2-benzyloxyethyl)-3-ethyl-2-azetidinone is carried out as follows:

A mixture of 4-(2-benzyloxyethyl)-3-ethyl-2-azetidinone (11.65 g), 2-methoxypropene (7.1 ml), borontrifluoride etherate (0.5 ml) in anhydrous toluene (87 ml) is stirred at room temperature for 3½ hours. Then potassium t-butoxide (3.13 g) is added at room temperature monitoring the epimerization by means of gas-chromatographic assays. After one hour, 40% acetic acid (30 ml) is added and the mixture is heated to 75° C. for two hours and allowed to stand at room temperature overnight. The aqueous acidic phase which separates is extracted with toluene (two 30-ml portions) and the toluene extracts are combined, dried over $Na_2SO_4$ and concentrated to dryness under vacuum yielding 10.5 g of crude 4-(2-benzyloxoethyl)-3-ethyl-2-azetidinone which contains 90% of the trans-isomer (estimated by N.M.R.).

EXAMPLE 5

Resolution of trans-(±)-3-ethyl-4-oxo-2-azetidinacetic acid (I R=$CH_3$—$CH_2$—) with dextro and laevo-oxyphene (a) Salt of trans-(±)-3-ethyl-4-oxo-2-azetidinacetic acid with laevo oxyphene Trans-(±)-3-ethyl-4-oxo-2-azetidinacetic acid (15.7 g, 0.1 mole) is added to a solution of 1-oxyphene (28.35 g, 0.1 mole) in refluxing acetone (176 ml). The resulting solution is allowed to stand at room temperature for four hours, at about 3° C. for 24 hours and then at about −25° C. for 16 hours. The precipitate which forms is recovered by vacuum filtration, washed with ice-cooled acetone and dried under vacuum at 40° C. for one hour to yield 11.15 g of a salt characterized by an $[\alpha]_D = -4.5°$ (C=1 in $CHCl_3$). This salt is crystallized twice from acetone (45 and 40 ml respectively) keeping the solutions at room temperature for one hour, then at about 3° C. for four hours and finally at about −25° C. for 16 hours. The salt of trans-(+)-3-ethyl-4-oxo-2-azetidinacetic acid with laevo-oxyphene thus obtained (7.04 g) has m.p. of 124°–24.5° C. and $[\alpha]_D = +4.3°$ (C=1 in $CHCl_3$).

(b) Trans-(+)-3-ethyl-4-oxo-2-azetidinacetic acid

To a stirred mixture of the above salt (7.04 g), water (18 ml) and diethyl ether (40 ml), a solution of 1N NaOH (15.8 ml) is gradually added to bring the pH to about 8.3. The aqueous phase is separated and extracted with diethyl ether (two 20-ml portions). The ethereal layers are washed with water (two 10-ml portions), dried over Na$_2$SO$_4$ and concentrated to dryness yielding l-oxyphene (4.29 g, 94.2%).

The combined aqueous layers are saturated with (NH$_4$)$_2$SO$_4$ (40 g), stirred for a few minutes and acidified to pH 3.7 with 2N H$_2$SO$_4$ (about 8 ml). The mixture is extracted with ethyl acetate (180 ml followed by four 60-ml portions) and the combined extracts are dried over MgSO$_4$ concentrated to about 15 ml at room temperature, under vacuum, and kept at about $-25°$ C. for 18 hours. The solid is collected by filtration and dried under vacuum at room temperature to yield 2.32 g of trans-(+)-3-ethyl-4-oxo-2-azetidinacetic acid. M.p. 113°–15° C.; $[\alpha]_D = +16°$ (C=1 in EtOH)-Enantiomeric purity: ~98%.

By carrying out the resolution essentially as described above but crystallizing the salt of trans-(+)-3-ethyl-4-oxo-2-azetidinacetic acid with l-oxyphene once more from acetone, pure trans-(+)-3-ethyl-4-oxo-2-azetidinacetic acid characterized by $[\alpha]_D = +16.6°$ (C=1 in EtOH) is obtained.

(c) Crude trans (−)-3-ethyl-4-oxo-2-azetidinacetic acid

The mother liquors deriving from the salification step described in (a) above are evaporated to dryness and the crude laevo acid is recovered by following the method described in (b) above. The ethyl acetate solution is distilled to dryness under vacuum at room temperature to yield 10.45 g of crude laevo acid. $[\alpha]_D = -3.81°$ (C=1 in EtOH).

(d) Salt of trans-(−)-3-ethyl-4-oxo-2-azetidinacetic acid with dextro-oxyphene

The crude laevo acid obtained in (c) above (10.45 g, 66.5 mmole) is added to a solution of dextro-oxyphene (11.82 g, 66.5 mmole) in hot acetone (117 ml). This solution is allowed to stand at room temperature for 4 hours and at about 4° C. for 18 hours. The solid which precipitates is recovered by filtration and dried under vacuum at 40° C. for one hour to yield 8.85 g of a salt characterized by m.p. 120°–21° C. and $[\alpha]_D = +2.44°$ (C=1 in CHCl$_3$). This salt is crystallized twice from acetone (44 and 30 ml respectively) keeping the solutions at room temperature for 4 hours and at about 3° C. for 18 hours. The salt of trans-(−)-3-ethyl-4-oxo-2-azetidinacetic acid with d-oxyphene, thus obtained, (5.45 g) has m.p. 124°–25° C. and $[\alpha]_D = -4.35°$ (C=1 in CHCl$_3$).

(e) Trans-(−)-3-ethyl-4-oxo-2-azetidinacetic acid

The free acid is obtained from the corresponding d-oxyphene salt (5.45 g) by following the procedure described in (b) above. Yield: 1.79 g of trans-(−)-3-ethyl-4-oxo-2-azetidinacetic acid characterized by a m.p. of 113°–15° C. and $[\alpha]_D = -16°$ (C=1 in EtOH). Enantiomeric purity: ~98%.

Pure trans-(−)-3-ethyl-4-oxo-2-azetidinacetic acid recovered after a further crystallization of the d-oxyphene salt prepared in (d) above from acetone, has $[\alpha]_D = -16.6°$ (C=1 in EtOH).

(f) Quasi-racemic acid

The mother liquors deriving from the crystallizations described in steps (a) and (d) are combined and evaporated to dryness and the acid (7.3 g) is recovered following the method described in (b) above. M.p. 103°–05° C., $[\alpha]_D = +1.2°$ (C=1% in EtOH).

This quasi-racemic acid is submitted to a recycle following the same alternate salification process with dextro and laevo-oxyphene previously described. A second crop of trans-(+)-3-ethyl-4-oxo-2-azetidinacetic acid (1.42 g), m.p. 113°–15° C., $[\alpha]_D = +16°$ (C=1 in EtOH) is obtained and 4.4 g of quasi-racemic acid (m.p. 102°–104° C., $[\alpha]_D = +0.7°$ (C=1 in EtOH) are recovered. Thus, the overall yields in trans-(+)-3-ethyl-4-oxo-2-azetidinacetic acid, after resolution followed by a recycle of the recovered quasi-racemic acid are ~24% based on the starting racemic acid.

EXAMPLE 6

Resolution of trans-(±)-3-ethyl-4-oxo-2-azetidinacetic acid (I R=CH$_3$—CH$_2$—) with cinchonidine (a) Salt of trans-(−)-3-ethyl-4-oxo-2-azetidinacetic acid with cinchonidine Trans-(±)-3-ethyl-4-oxo-2-azetidinacetic acid (10.21 g, 65 mmole) is added to a solution of cinchonidine (19.1 g, 65 mmole) in isopropyl alcohol (70 ml) heated to about 50° C. The clear solution is then diluted with acetone (140 ml) and allowed to stand at room temperature for four hours and at about 4° C. for nineteen hours. The white crystals which separate, are collected, washed with acetone (20 ml) and dried under vacuum for two hours at 40° C. to yield 10 g of a salt characterized by m.p. 145°–51° and $[\alpha]_D = -85°$ (C=1 in EtOH). This salt is crystallized twice from isopropyl alcohol (23 ml) and acetone (46 ml), keeping the solutions for a few hours at room temperature and then at about 4° C. until the crystallization is substantially complete (24–48 hours)—Yield: 6.1 g (20.8%) of pure cinchonidine salt of trans-(−)-3-ethyl-4-oxo-2-azetidinacetic acid characterized by a m.p. of 166°–67° C. and $[\alpha]_D = -94.7°$ (C=1 in EtOH).

(b) Trans-(−)-3-ethyl-4-oxo-2-azetidinacetic acid

A suspension of the above cinchonidine salt (6.1 g, 13.52 mmole) in water (16 ml) is stirred for a few minutes, than 1N sodium hydroxide (13.5 ml) is added to bring the pH to 8.3. The obtained slurry is extracted with chloroform (30 ml plus two 15-ml portions) and the combined organic extracts are washed with water (two 10-ml portions). The aqueous phase and washes are combined, saturated with ammonium sulfate (50 g) and acidified to pH 3.7 by the addition of 2N H$_2$SO$_4$ (~7 ml). The mixture is extracted with ethyl acetate (80 ml plus four 50-ml portions) and the combined organic extracts are dried over Na$_2$SO$_4$ and concentrated to a small volume (about 10 ml), at room temperature, under vacuum. After standing overnight at about 4° C., the solid is recovered by filtration and dried under vacuum at room temperature to yield 1.86 g of pure trans-(−)-3-ethyl-4-oxo-2-azetidinacetic acid with m.p. 113°–15° C. and $[\alpha]_D = -16.7°$ (C=1 in EtOH).

(c) Salt of trans-(+)-3-ethyl-4-oxo-2-azetidinacetic acid with cinchonidine

The mother liquors deriving from the salification step described under (a) above, are concentrated under vacuum at room temperature to a syrupy consistence. This residue is taken up with acetone (50 ml) and the mixture is boiled for a few minutes until some solid separates. After standing overnight at about 3° C. the crystalline precipitate is collected and dried to yield 9.05 g of the crude salt characterized by a m.p. of 149°–51° C. and $[\alpha]_D = -80.4°$ (C=1 in EtOH). This product is crystallized twice from a mixture isopropyl alcohol/acetone ½, first with a volume of 120 ml and then with 45 ml, yielding 2.05 g (7%) of the pure cinchonidine salt of trans-(+)-3-ethyl-4-oxo-2-azetidinacetic acid. M.p. 159°–160° C., $[\alpha]_D = -76°$ (C=1 in EtOH).

(d) Trans-(+)-3-ethyl-4-oxo-2-azetidinacetic acid

The free acid is obtained from the corresponding cinchonidine salt by following the same method used for the laevo acid and described in paragraph (b) above (0.61 g). M.p. 112°–14° C., $[\alpha]_D = +15.9°$ (C=1 in EtOH). Enantiomeric purity : 97.9%.

EXAMPLE 7

Cis-(±)-3-ethyl-4-oxo-2-azetidinacetic acid (a) Cis-(±)-4-[2-(acetyloxy)ethenyl]-3-ethyl-2-azetidinone (Chart I VI R=CH$_3$—CH$_2$—)

The mixture of four isomers of 4-[2-(acetyloxy)ethenyl]-3-ethyl-2-azetidinone (40 g, $2.18 \times 10^{-1}$ mole) obtained in example 1(b), is taken up with peroxide-free isopropyl ether (40 ml) and the mixture is stirred at room temperature for about 4 hours and allowed to stand at about 3° C. for 8 hours. The solid is recovered by filtration and dried under vacuum to yield 4.4 g (11%) of the cis isomers pair. M.p. 102° C. The N.M.R. and I.R. spectra confirm the assigned structure.

(b) Cis-(±)-3-ethyl-4-(2-hydroxyethyl)-2-azetidinone (Chart I, II, R=CH$_3$—CH$_2$—)

Cis-(±)-4-[2-(acetoxy)ethenyl]-3-ethyl-2-azetidinone (20 g, 0.109 mole) is dissolved in ethyl acetate (150 ml) warming the mixture until complete solution. Then, 10% Palladium on carbon catalyst (1 g) is added and the starting compound is hydrogenated at room temperature and with a pressure of 3 atmosphere of hydrogen gas, in a Parr autoclave. After six hours the autoclave is discharged and the catalyst is filtered. The solvent is evaporated and the crude cis-(±)-4-[2-(acetoxy)ethyl]-3-ethyl-2-azetidinone (20 g) thus obtained is placed in a 250-ml flask equipped with a calcium chloride drying tube and a dry nitrogen inlet tube, charged with potassium carbonate (5 g, $3.6 \times 10^{-2}$ mole) and anhydrous methanol (130 ml). The reaction mixture is stirred at room temperature for about one hour, then it is neutralized by the addition of citric acid (5.5 g, $2.9 \times 10^{-2}$ mole), and filtered through a Büchner funnel. The solid on filter is washed with methanol (2×10 ml) and the filtrate plus the methanol washings are concentrated to dryness under reduced pressure. The residue thus obtained is dissolved in water (100 ml) and extracted with methylene chloride (3×20 ml). The combined methylene chloride extracts are washed with water (2×15 ml) and then discarded. The aqueous solutions are combined, saturated with ammonium sulfate and extracted with five 20-ml portions of ethyl acetate. The combined ethyl acetate extracts are dried over magnesium sulfate and the solvent is removed under reduced pressure to yield 10.4 g (67.3%) of cis-(±)-3-ethyl-4-(2-hydroxyethyl)-2-azetidinone II as a thick oil, sufficiently pure for the next step.

(c) Cis-(±)-3-ethyl-4-oxo-2-azetidinacetic acid (I, R=CH$_3$—CH$_2$—)

Crude cis-(±)-3-ethyl-4-(2-hydroxyethyl)-2-azetidinone (7 g, 0.049 mole) obtained according to step (b) above is added to a solution of sodium phosphate dibasic dodecahydrate (6 g) and sodium phosphate monobasic monohydrate (3.6 g) in water (80 ml). After 15 minutes with stirring, the pH of the solution is adjusted to 6.6 by the dropwise addition of a 10% NaOH solution, the temperature is lowered to 5°–10° C., and potassium permanganate (10.75 g, 0.068 mole) is added. The temperature of the reaction is kept at 10°–15° C. by means of an ice bath, and the pH is maintained in the range 6.6–7.5 by the dropwise addition of 10% sulfuric acid (7 ml). After eight hours the temperature is lowered to about 3°–4° C. and the reaction mixture is allowed to stand at this temperature overnight. Then, the excess of permangate is destroyed by the dropwise addition of an aqueous solution saturated with sodium meta-bisulfite, and manganese dioxide is removed by vacuum filtration on Celite and washed with water (30 ml). The aqueous solution is saturated with ammonium sulfate (70.6 g in 100 ml of cold water) and the pH is adjusted to 3.5 by the addition of 10% sulfuric acid. The aqueous acidic solution is extracted with ethyl acetate (100 ml plus four 50-ml portions) and the combined extracts are dried over mgSO$_4$, filtered and concentrated to a 30-ml volume under reduced pressure and at 35° C. Crystallization is allowed to begin at room temperature and then to proceed for 8 hours at 3°–4° C. The precipitate is recovered by filtration and dried under vacuum to yield 1.65 g (21.4%) of crystalline cis acid. M.p. 102° C. (with decomposition). The I.R. and N.M.R. spectra confirm the assigned structure. In particular they show the following characteristics: I.R. spectrum (nujol): 3350($\nu$ NH),3500–2200($\nu$ OH acid), 1750($\nu$ CO lactam),1700($\nu$ CO acid),1210 ($\nu$ C-O) cm$^{-1}$ N.M.R. (270 MHz, $\delta$ (ppm)) in CDCl$_3$: 1.08 (3H, t, C$\underline{H}_3$—CH$_2$—), 1.5–1.9 (2H, m, CH$_3$—C$\underline{H}_2$—), 2.6–2.7 (2H, 2dd, J$_{gem}$=17 Hz, J$_{vic}$=10–4 Hz,

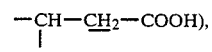

3.2 (1H, ddd, J$_{cis}$=5.5 Hz,

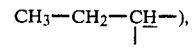

4.0 (1H, ddd, J$_{cis}$=5.5 Hz,

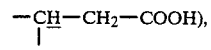

7.1 (1H, s,N$\underline{H}$), COOH not determined.

EXAMPLE 8

Trans-(±)-3-[[2-(acetylamino)ethyl]thio]-6-ethyl-7-oxo-1-azabicyclo[3.2.0]hept-2-en-2-carboxylic acid sodium salt (Chart III XVIII R=CH$_3$CH$_2$—R'''=CH$_3$CONH—CH$_2$—CH$_2$—)

(a) Preparation of trans(±)-3-ethyl-4,$\beta$-dioxo-2-azetidinbutanoic acid, (4-nitrophenyl)methyl ester (XIII R=CH$_3$CH$_2$—R$_4$=

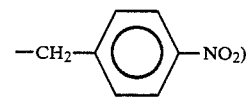

A mixture of 3-ethyl-4-oxo-2-azetidineacetic acid (21 g), 1,1'-carbonyldiimidazole (24.32 g) and anhydrous tetrahydrofuran (360 ml) is stirred for 2½ hours at room temperature, then mono-p-nitrobenzylmalonate magnesium salt (80.1 g) is added and stirring is continued for 19 hours at room temperature. The mixture is poured into 5% HCl (600 ml) and extracted with methylene chloride (four 450-ml portions). The organic extracts are combined, washed with 10% KHCO$_3$ (two 200-ml portions), with brine (200 ml) and dried over MgSO$_4$. The solvent is removed under vacuum and the obtained residue is triturated with diethyl ether (60 ml), filtered and dried in vacuo at room temperature yielding the desired keto-ester XIII (R=CH$_3$CH$_2$—) (31.6 g) which melts at 88°-90° C.

The I.R. and N.M.R. spectra show the following characteristics:

I.R.(nujol,cm$^{-1}$):3400($\nu$NH),1750($\nu$ C=O lactam and ester), 1725 ($\nu$ C=O ketone), 1520 and 1320 ($\nu$ NO$_2$), 1225 ($\nu$C—O—C), 850 ($\gamma$CH arom.).

NMR (CDCl$_3$, 270 MHz, $\delta$): 0.99 (t, 3H, $J_{CH_2\text{-}CH_3}$=7 Hz, —CH$_3$), 1.74 (m, 2H, CH$_2$—CH$_3$), 2.72 (d.t., 1H, $J_{H3\text{-}H4}$=2 Hz, $J_{H3\text{-}CH_2}$=6.5 Hz, H$_3$), 2.85-3.01 (2dd, 2H, $J_{gem}$=18 Hz, $J_{H4\text{-}CH_2}$=9-4 Hz,CH—CH$_2$CO), 3.56 (s, 2H, —CO—CH$_2$—CO), 3.63 (b.d.d.d., 1H, H$_4$), 5.11 (s,2H, OCH$_2$), 6.27 (b.d.,1H, NH), 7.45 (d,2H, $J_{ortho}$=9 Hz, C—Ar), 8.14 (d,2H, N—Ar).

Preparation of mono-p-nitrobenzylmalonate magnesium salt

First step: Preparation of Meldrum's acid

A 1-l three-necked flask fitted with a mechanical stirrer and a thermometer is charged with 208 g of malonic acid (2 moles) and 260 ml of isopropenyl acetate (236 moles). The content of the flask is cooled to 20° C. and 2 ml of sulphuric acid are added in 10 minutes. The temperature in the flask is kept below 40° C. for the following 90 minutes. The content is then transferred into a 1-l Erlenmeyer flask and left at room temperature overnight. The dark solution is seeded, stored in the refrigerator for 6 hours and the resulting crystals filtered under vacuum and washed three times with sufficient water to cover the cake. The yield of air dried product is 213.65 g (74%), m.p. 93°-96° C.

A second crop is obtained by leaving the mother liquor in the refrigerator overnight (22.30 g, 7.8%). Total yield 235.95 (81.8%).

Second step: Preparation of mono-p-nitrobenzylmalonate

A solution of 48 g of Meldrum's acid (0.333 moles) and 48 g of p-nitrobenzyl alcohol (0.314 moles) in 200 ml of acetonitrile is heated for 15 hours in a 500-ml flask kept in an oil bath at 100° C.

The solvent is then evaporated in vacuo and the residue is dissolved in methylene chloride (50 ml) and tert-butylmethyl ether (500 ml). After concentrating to 300 ml, the solution is stored in the refrigerator for 6 hours; the resulting solid is collected under vacuum filtration, washed with cold t-butyl methyl ether (50 ml) and air dried (50.46 g; 67%; m.p. 97°-98° C.). Concentration of the mother liquor to 100 ml affords after one night in the refrigerator a second crop (10.9 g, 14.5%; m.p. 97°-99° C.). The mother liquor is extracted with 10% potassium bicarbonate (100 ml), and after filtration on celite the aqueous phase is acidified to pH 3 with 8% hydrochloric acid. The resulting solid is filtered under vacuum, washed with a liberal amount of cold water and air dried. This third crop consists of 10.37 g (13.8%); M.p. 99°-100° C. Total yield 71.73 g, 95%.

The mono-para-nitrobenzylmalonate has been also prepared by direct esterification of malonic acid with para-nitro-benzyl chloride according to the following procedure: A solution of dry malonic acid (104 g, 1 mole) in dimethylformamide (290 ml) is treated at 15°-20° C. with triethylamine (139 ml, 1 mole). Under stirring, a solution of para-nitrobenzyl chloride (171.6 g, 1 mole) in dimethylformamide (400 ml) is added, followed by solid potassium iodide (25 g, 0.15 moles). After three days under stirring, the reaction mixture is diluted with methylene chloride (1 l) and slowly treated with 10% solution of potassium bicarbonate (2 l). The aqueous phase is acidified with 18% hydrochloric acid (420 ml) and the precipitate is filtered under vacuum, washed with water and dried to yield 70 g (29.3%) of mono-para-nitrobenzylmalonate; M.p. 99°-101° C.

Third step: Preparation of magnesium mono-p-nitrobenzylmalonate

A dry 3-l flask equipped with a mechanical stirrer is charged with 145.85 g of mono-p-nitrobenzylmalonate (0.61 moles) and 1365 ml of anhydrous tetrahydrofuran. After 15 minutes 35.4 g of magnesium ethoxide (0.31 moles) are added and the reaction mixture is stirred for two hours. The resulting clear solution is then added over a period of one hour to 2 liters of ethyl ether kept at 0° C. by an ice bath. After a further hour at 0° C. the resulting solid is filtered under vacuum and dried in vacuo to yield 144 g (94%) of magnesium mono-p-nitrobenzylmalonate.

(b) Preparation of trans-($\pm$)-$\alpha$-diazo-3-ethyl-4,$\beta$-dioxo-2-azetidinebutanoic acid, (4-nitrophenyl)methyl ester (XIV R=CH$_3$CH$_2$— R$_4$=

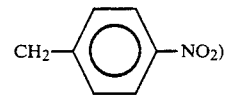

To a mixture of the keto ester obtained in step (a) above (30 g), p-carboxybenzenesulfonylazide (22.5 g) and acetonitrile (300 ml), cooled to 5° C., triethylamine (42 ml) is added drop by drop over a period of fifteen minutes. When about one half of the triethylamine has been added, a clear solution results from which a white solid soon precipitates. The temperature is then allowed to rise at about 20° C. in half an hour. The white solid is filtered and washed with acetonitrile (50 ml). The combined solutions are evaporated in vacuo at room temperature and the residue is dissolved in methylene chloride (300 ml), washed with 8% NaHCO$_3$ (100 ml) and with water (100 ml). The organic phase is dried over MgSO$_4$ and concentrated in vacuo to a syrupy consistence. Diethyl ether (250 ml) is slowly added with magnetic stirring and stirring is continued for one hour at 0° C. The product is collected under vacuum filtration and dried in vacuo at room temperature yielding 29.16 g of the desired diazo-keto ester XIV (R=CH$_3$CH$_2$—) which melts at 115°-18° C.

The I.R. and N.M.R. spectra show the following characteristics:

I.R. (nujol,cm$^{-1}$): 3280 ($\nu$ NH), 2170 ($\nu$C=N$_2$), 1760 ($\nu$C=O lactam), 1750 ($\nu$C=O ester), 1725 ($\nu$C=O ketone), 1525 and 1340 ($\nu$NO$_2$), 1225 ($\nu$C—O—C) and 850 ($\gamma$CH arom.)

NMR (CDCl$_3$, 270 MHz, $\delta$): 1.01 (t,3H, $J_{CH_2\text{-}CH_3}$=7 Hz, —CH$_3$), 1.76 (m,2H,$J_{H3\text{-}CH_2}$=6.5 Hz, CH$_2$—CH$_3$), 2.80 (d.t,1H, $J_{H3\text{-}H4}$=2 Hz, H$_3$), 3.03-3.33, (2dd,2H, $J_{gem}$=17 Hz, $J_{H4\text{-}CH_2}$=9-4 Hz, CH$_2$CO), 3.67 (bddd, 1H, H$_4$), 5.31 (s,2H, CH$_2$O); 6.02 (bd,1H,NH), 7.49 (d,2H, $J_{ortho}$=9 Hz, C—Ar), 8.12 (d,2H,N—Ar)

(c) Preparation of trans-($\pm$)-6-ethyl-3,7-dioxo-1-azabicyclo [3.2.0]heptan-2-carboxylic acid, (4-nitrophenyl)methyl ester (XV R=CH$_3$CH$_2$— R$_4$=

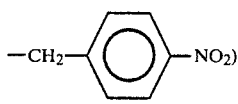

A solution of trans(±)-α-diazo-3-ethyl-4,β-dioxo-2-azetidinebutanoic acid, (4-nitrophenyl)methyl ester (30 g) prepared as described in step (b) above in 1,2-dichloroethane (250 ml) is added dropwise into a solution of rhodium acetate (0.3 g) in 1,2-dichloroethane (50 ml) heated to the reflux temperature. The mixture is refluxed for additional 30 minutes while the progress of the reaction is followed by the nitrogen evolution and thin layer chromatography on silicagel plates eluting with ethyl acetate:hexane 6:4. The reaction mixture is then cooled to 20° C., washed with water (two 100-ml portions), dried over MgSO$_4$ and evaporated to dryness under reduced pressure.

The residue is dissolved in methylene chloride (20 ml) and the product is precipitated by slow addition of diethyl ether (150 ml) under magnetic stirring and cooling. After one hour, the solid is collected under vacuum and dried in vacuo at room temperature yielding 25.7 g (91%) of trans(±)-6-ethyl-3,7-dioxo-1-azabicyclo[3.2.0]heptan-2-carboxylic acid, (4-p-nitrophenyl)methyl ester; M.p. 106°-109° C.

The I.R. and N.M.R. spectra show the following characteristics:

I.R. (nujol, cm$^{-1}$): 1780 ($\nu$C=O lactam), 1775 ($\nu$C=O ketone), 1755 ($\nu$C=O ester), 1525 and 1320 ($\nu$NO$_2$), 1240 ($\nu$C—O—C) and 845 ($\gamma$CH arom.)

NMR (CDCl$_3$, 270 MHz,δ): 1.10 (t,3H,J=7 Hz, —CH$_3$), 1.93 (m,2H, CH$_2$—CH$_3$), CH$_2$—CH$_3$, 2.45–2.88 (2dd,2H,J$_{gem}$=19 Hz, J$_{H5-CH2(4)}$=8—7 Hz, H$_4$ and H$_4'$), 3.12 (ddd, 1H, J$_{H5-H6}$=2 Hz, J$_{H6-CH2}$=7—8 Hz, H$_6$), 3.87 (ddd,1H,H$_5$), 4.72 (s,1H,H$_2$), 5.22–5.30 (2d,2H,J$_{gem}$=13.5 Hz, CH$_2$O), 7.48 (d,2H, J$_{ortho}$=9 Hz, C—Ar), 8.18 (d,2H,N—Ar).

(d) Preparation of trans (±)-3-[[2-(acetylamino)ethyl]thio]-6-ethyl-7-oxo-1-azabicyclo[3.2.0]hept-2-ene-2-carboxylic acid, (4-nitrophenyl)methyl ester (XVII, R=CH$_3$CH$_2$—, R'''=CH$_3$CONH—CH$_2$—CH$_2$—, R$_4$=

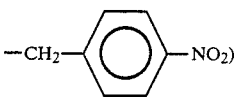

A solution of the bicyclic keto ester obtained in step (c) above (XV R=CH$_3$CH$_2$—) (2.49 g) in acetonitrile (15 ml) is cooled to 0° C. and diisopropylethylamine (1.42 ml) is added. Then chlorodiphenylphosphate (1.72 ml) is added drop by drop keeping the temperature at 0°/−2° C. Stirring is continued for 15 minutes at 0° C., after which thin layer chromatography confirms the complete transformation of the bicyclic keto ester XV into the enol phosphate derivative XVI (R=CH$_3$CH$_2$—). An additional portion of diisopropylethylamine (1.55 ml) is added followed by the slow addition of N-acetylcysteamine (1.07 g) dissolved in acetonitrile (5 ml). The reaction mixture is then stirred at 0° C. for 30 minutes and the solid which precipitates is filtered, washed with cold acetonitrile (10 ml) and diethyl ether (20 ml), and dried in vacuo at room temperature yielding 2.03 g of trans (±)-3-[[2-(acetylamino)ethyl]-6-ethyl-7-oxo-1-azabicyclo[3.2.0]hept-2-ene-2-carboxylic acid, (4-nitrophenyl)methyl ester which melts at 174°-76° C. Additional 0.46 g of equally pure product is obtained on cooling the filtrate to −20° C. for 2 hours.

The I.R., U.V. and NMR spectra show the following characteristics:

I.R. (CDCl$_3$, cm$^{-1}$): 3480 ($\nu$NH), 1780 ($\nu$C=O lactam), 1700 ($\nu$C=O ester), 1680 and 1550 (amide I and II), 1525 and 1340 ($\nu$NO$_2$), 1200 ($\nu$C—O—C)

U.V. $\lambda_{max}^{MeOH}$=317 nm, $\epsilon$=7,110

NMR (CDCl$_3$, 270 MHz, δ): 1.07 (t,3H,J$_{CH2-CH3}$=7 Hz,CH$_2$—CH$_3$), 1.87 (m,2H,J$_{H6-CH2}$=7 Hz, CHHD 2—CH$_3$), 2.02 (s,3H,COCH$_3$), 2.90–3.04 (2ddd, 2H,J$_{gem}$=12.5 Hz, J$_{CH2-CH2}$=6.7 Hz,CH$_2$S), 3.10–3.44 (2dd,2H,J$_{gem}$=19 Hz, J$_{CH2(4)-H5}$=8–9 Hz, H$_4$ and H$_4'$), 3.14 (d.t,1H,J$_{H5-H6}$=2.5 Hz, H$_6$), 3.99 (ddd,1H,H$_5$), 5.24–5.51 (2d,2H, J$_{gem}$=14 Hz,CH$_2$O), 5.91 (b,1H,NHCO), 7.66 (d,2H,J$_{ortho}$=8 Hz C—Ar), 8.22 (d,2H,N—Ar).

(e) Preparation of trans(±)-3-[[2-(acetylamino)ethyl]thio]-6-ethyl-7-oxo-1-azabicyclo[3.2.0]hept-2-en-2-carboxylic acid sodium salt (XVIII R=CH$_3$—CH$_2$—, R'''=CH$_3$CONHCH$_2$CH$_2$—,Me$^\oplus$=Na$^\oplus$)

A 500-ml flask is charged with a suspension of 10% palladium on carbon (0.65 g) in tetrahydrofuran (20 ml) and connected to a hydrogenation apparatus placed on an air driven magnetic stirrer and pre-hydrogenated for 30 minutes at room temperature and pressure. A solution of trans(±)-3-[[2-(acetylamino)ethyl)thio]-6-ethyl-7-oxo-1-azabicyclo[3.2.0]hept-2-ene-2-carboxylic acid (4-nitrophenyl)methyl ester (0.65 g) in tetrahydrofuran (60 ml) and 0.075M phosphate buffer pH 8 (20 ml) is added, followed by tetrahydrofuran (20 ml) and 0.075M phosphate buffer pH 8 (40 ml). The mixture is hydrogenated for one hour then the catalyst is removed under vacuum filtration on a double bed of 2 g of celite (lower) and 3 g of charcoal (upper) and washed with a 1:1 tetrahydrofuran/0.075M phosphate buffer mixture (30 ml). The organic solvent is distilled from the filtrate at 1–2 mmHg and room temperature and the dark aqueous solution is extracted with methylene chloride (50 ml followed by two 25-ml portions).

The organic layers are discarded and the aqueous phase is filtered again on a double bed of 2 g of celite and 3 g of charcoal. The filter is washed with 0.075M phosphate buffer pH 8 (20 ml) and the clean filtered solution is concentrated to 50 ml in vacuo at a temperature of 30°–35° C. The solution so obtained is desalted through a column (2.2×27 cm) packed with 90 ml of Amberlite XAD-2 and equilibrated with a 5 mM phosphate buffer pH 7.75, containing 0.5% of NaCl. The column is eluted with:

50 ml of the equilibrating phosphate buffer,
300 ml of water,
100 ml of 12.5% aqueous methanol,
200 ml of 25% aqueous methanol.

10-Ml fractions are collected and analyzed by HPLC. Fractions 21 to 58 are combined, concentrated in vacuo at a temperature lower than 35° C. up to 10 ml and lyophilized to obtain 0.133 g of the compound of the title.

The NMR spectrum shows the following characteristics:

NMR (D$_2$O, 270 MHz,TSP as internal reference, δ): 1.01 (t,3H,J$_{CH2-CH}$=7 Hz, CH$_2$—CH$_3$), 1.81 (m,2H,J$_{CH2-H6}$=7 Hz, CH$_2$—CH$_3$), 2.01 (s,3H,CO—CH$_3$), 2.91–2.98 (2dt,2H, J$_{gem}$=13.5 Hz, $J_{CH_2\text{-}CH_2}=6$ Hz, $CH_2\text{—S}$), 3.07–3.24 (2dd,2H,$J_{gem}=17.5$, $J_{CH_2(4)\text{-}H_5}=9\text{–}10$ Hz, $H_4$ and $H'_4$), 3.29 (d.t,1H, $J_{H_5\text{-}H_6}=2.5$ Hz,$H_6$) 3.41 (t,2H, C$\underline{H}_2$—NH); 4.02 (ddd,1H,$H_5$).

EXAMPLE 9

Trans-(+)-3-[[2-(acetylamino)ethyl]thio]-6-ethyl-7-oxo-1-azabicyclo[3.2.0]-hept-2-en-2-carboxylic acid potassium salt (Chart III-XVIII R=CH$_3$—CH$_2$— R'''=CH$_3$—CONH—CH$_2$—CH$_2$—Me$^\oplus$=K$^\oplus$) (Antibiotic PS-5 potassium salt)

The compound of the title is obtained by following essentially the same procedure as in example 8 but starting from the corresponding trans-(+)-3-ethyl-4-oxo-2-azetidinacetic acid; $[\alpha]_D=+74.9°$ (C=1 in H$_2$O). During the course of the reaction the following intermediates are obtained:

(a) Trans-(+)-3-ethyl-4,β-dioxo-2-azetidin-butanoic acid, (4-nitrophenyl)methyl ester (XIII R=CH$_3$CH$_2$— R$_4$=

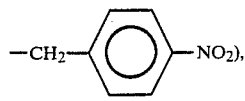

m.p. 85°–86° C., $[\alpha]_D=+15.9°$ (C=1 in EtOH), $[\alpha]_D=+40.7°$ (C=1 in CHCl$_3$).

(b) Trans-(+)-α-diazo-3-ethyl-4,β-dioxo-2-azetidin-butanoic acid, (4-nitrophenyl)methyl ester (XIV R=CH$_3$CH$_2$— R$_4$=

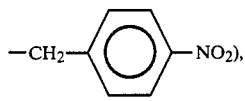

m.p. 111°–12° C., $[\alpha]_D=+28.4°$ (C=1 in EtOH), $[\alpha]_D=+64.7°$ (C=1 in CHCl$_3$)

(c) Trans-(+)-6-ethyl-3,7-dioxo-1-azabicyclo[3.2.0]heptan-2-carboxylic acid, (4-nitrophenyl)methyl ester (XV R=CH$_3$CH$_2$— R$_4$=

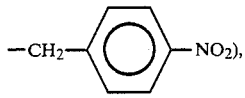

m.p. 79°–80° C., $[\alpha]_D=+231°$ (C=1 in EtOH), $[\alpha]_D=+224.1°$ (C=1 in CHCl$_3$)

(d) Trans-(+)-3-[[2-(acetylamino)ethyl]thio]-6-ethyl-7-oxo-1-azabicyclo[3.2.0]hept-2-ene-2-carboxylic acid, (4-nitrophenyl)methyl ester (XVII R=CH$_3$—CH$_2$— R'''=CH$_3$CONH—CH$_2$CH$_2$— R$_4$=

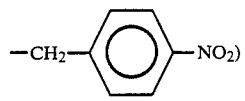

m.p. 172°–74° C., $[\alpha]_D=+71.5°$ (C=1 in CHCl$_3$).

EXAMPLE 10

Trans-(−)-3-[[2-(acetylamino)ethyl]thio]-6-ethyl-7-oxo-1-azabicyclo[3.2.0]hept-2-ene-2-carboxylic acid potassium salt (Chart III-XVIII R=CH$_3$CH$_2$— R'''=CH$_3$CONH—CH$_2$CH$_2$—,Me$^\oplus$=K$^\oplus$)

The compound of the title is obtained by following essentially the same procedure described in example 8 but starting from the corresponding trans-(−)-3-ethyl-4-oxo-2-azetidinacetic acid. $[\alpha]_D=-74.7°$ (C=1 in H$_2$O).

During the course of the reaction the following intermediates are obtained:

(a) Trans-(−)-3-ethyl-4,β-dioxo-2-azetidin-butanoic acid, (4-nitrophenyl)methyl ester (XIII R=CH$_3$CH$_2$— R$_4$=

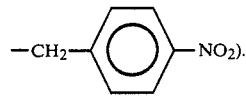

M.p. 85°–86° C., $[\alpha]_D=-16.1°$ (C=1 in EtOH).

(b) Trans-(−)-α-diazo-3-ethyl-4,β-dioxo-2-azetidin-butanoic acid, (4-nitrophenyl)methyl ester (XIV R=CH$_3$CH$_2$— R$_4$=

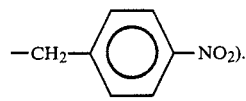

M.p. 110°–11° C., $[\alpha]_D=-27.5°$ (C=1 in EtOH).

(c) Trans-(−)-6-ethyl-3,7-dioxo-1-azabicyclo[3.2.0]heptan-2-carboxylic acid, (4-nitrophenyl)methyl ester (XV R=CH$_3$CH$_2$— R$_4$=

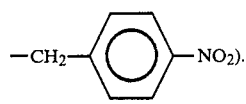

M.P. 79°–81° C., $[\alpha]_D=-228.2°$ (C=1 in CHCl$_3$)

(d) Trans-(−)-3-[[2-(acetylamino)ethyl]thio]-6-ethyl-7-oxo-1-azabicyclo[3.2.0]hept-2-ene-2-carboxylic acid, (4-nitrophenyl)methyl ester (XVII R=CH$_3$CH$_2$—, R'''=CH$_3$CO—NH—CH$_2$CH$_2$— R$_4$=

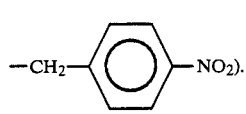

M.p. 163°–65° C., $[\alpha]_D=-69.8°$ (C=1 in CHCl$_3$).

EXAMPLE 11

Cis-(±)-3-[[2-(acetylamino)ethyl]thio]-6-ethyl-7-oxo-1-azabicyclo[3.2.0]hept-2-en-2-carboxylic acid potassium salt (Chart III XVIII: R=CH$_3$—CH$_2$—; R'''=CH$_3$—CONH—CH$_2$CH$_2$—; Me$^\oplus$=K$^\oplus$)

The compound of the title is obtained by following essentially the same procedure described in example 8, but starting from the cis isomers of 3-ethyl-4-oxo-2-azetidineacetic acid prepared in example 7.

The N.M.R. spectrum shows the following characteristics (D₂O, 270 MHZ, TSP as internal reference, δ(ppm)): 1.0 (t, 3H, —CH₂—CH₃), 1.6-1.9(2ddq, 2H, CH₃—CH₂—), 2.0 (s, 3H, —COCH₃), 2.8-3.2 (m, 4H,

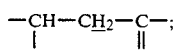

S—CH₂—CH₂—NH—), 3.43 (m, 2H, S—CH₂—CH₂), 3.6 (ddd, 1H,

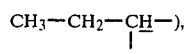

4.3 (ddd, 1H, J$_{cis}$=5.5 Hz

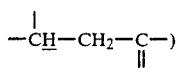

During the course of the reaction the following intermediates are isolated:

(a) Cis-(±)-3-ethyl-4,β-dioxo-2-azetidin-butanoic acid, (4-nitrophenyl)methyl ester (XIII, R=CH₃—CH₂— R₄=

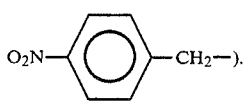

M.p. 121° C. I.R. (nujol): 3250 (νNH), 1725 (νCO lactam and ester), 1700 (νCO ketone); 1625 (νC—H arom.), 1520 and 1350 (νNO₂), 1230 (νC—O), 860 (νC—N), 830 (γC—H arom.) cm⁻¹.

N.M.R. (CDCl₃, 270 MHz, δ): 1.1 (t, 3H, —CH₂—CH₃), 1.4-1.9 (m, 2H, —CH₂—CH₃), 2.77-3.10 (2dd, 2H, J$_{gem}$=18 Hz, J$_{vic}$=9.5-4 Hz

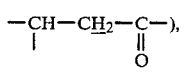

3.2 (ddd, 1H, J$_{cis}$=5.5 Hz,

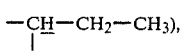

3.6 (s, 2H,

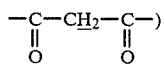

4.2 (ddd, 1H, J$_{cis}$=5.5 Hz,

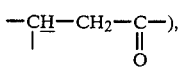

5.3 (s, 2H, —O—CH₂—φ), 6.0 (s, 1H, NH), 7.6 (d, 2H,

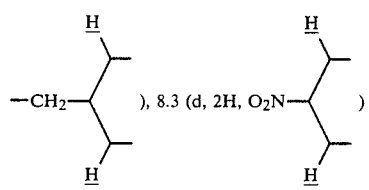

), 8.3 (d, 2H, O₂N—

(b) Cis-(±)-α-diazo-3-ethyl-4,β-dioxo-2-azetidinebutanoic acid, (4-nitrophenyl)methyl ester (XIV R=CH₃—CH₂—, R₄=

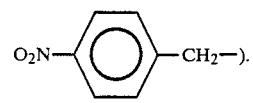

Two crystalline forms with m.p. 100° and 120°
I.R. (nujol): 3400 (νNH), 2175 (νC=N₂), 1750 (νCO lactam) 1700 (νCO ester), 1670 (νC=O ketone), 1520 and 1340 (νNO₂), 1205 (νC—O), 850 (νC—N), 830 (γC—H arom.) cm⁻¹.

N.M.R. (CDCl₃, 270 MHz, δ): 1.09 (t, 3H, CH₃—CH₂—), 1.5-1.9 (m, 2H, CH₃—CH₂—), 3.0-3.3 (2dd, 2H, J$_{gem}$=18 Hz, J$_{vic}$=10-3.5 Hz

3.2 (ddd, 1H,

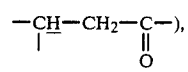

4.09 (ddd, 1H, J$_{cis}$=5.5 Hz,

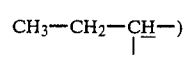

5.4 (s, 2H, —CH₂—φ), 6.07 (s, 1H, —NH—), 7.6 (d, 2H,

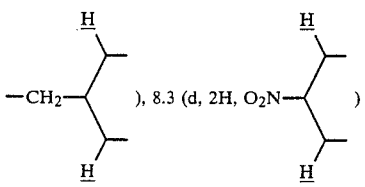

), 8.3 (d, 2H, O₂N—

(c) Cis-(±)-6-ethyl-3,7-dioxo-1-azabicyclo[3.2.0]heptan-2-carboxylic acid, (4-nitrophenyl)methyl ester (XV, R=CH₃—CH₂—, R₄=

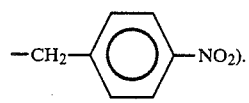

M.p. 128° C.
I.R. (CDCl₃): 1765 (νCO lactam and ketone), 1750 (νCO ester), 1610 (νC—H arom.), 1525 and 1350 (νNO₂), 1220 (νC—O) cm⁻¹.

N.M.R. (CDCl₃, 270 MHz, δ): 1.04 (t, 3H, CH₃—CH₂), 1.57 and 1.82 (2ddq, 2H, CH₃—C$\underline{H}$₂), 2.46 and 2.73 (2dd, 2H, J$_{gem}$=19 Hz, J$_{vic}$=8–7 Hz,

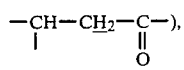

3.69 (ddd, 1H, J$_{cis}$=5.5 Hz,

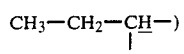

4.27 (ddd, 1H, J$_{cis}$=5.5 Hz,

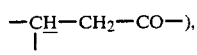

4.69 (s, 1H,

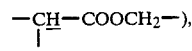

5.25 and 5.36 (dd, 2H, J$_{gem}$=13 Hz, —C$\underline{H}$₂ φ), 7.54 (d, 2H, J$_{ortho}$=8.5 Hz,

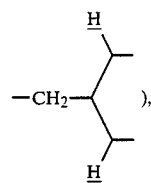

8.24 (d, 2H,

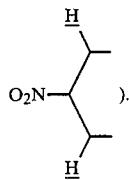

(d) Cis-(±)-3-[[2-(acetylamino)ethyl]thio]-6-ethyl-7-oxo-1-azabicyclo[3.2.0]hept-2-en-2-carboxylic acid, (4-nitrophenyl)methyl ester (XVII R=CH₃—CH₂—, R'''=CH₃CONH—CH₂CH₂—, R₄=

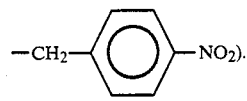

At the end of the reaction, carried out as described in example 8(d), the cis-racemate, unlike the trans one, does not crystallize out from the reaction mixture, therefore 200 ml of a mixture ethyl acetate/toluene 8/2 and 40 ml of phosphate buffer (pH 8) are added to the solution and the organic phase is separated, washed with water (40 ml) and dried over magnesium sulfate. After evaporating the solvent, the crude compound is triturated with diethyl ether (100 ml) which is then removed by filtration, and dried under vacuum yielding cis-(±)-3-[[2-(acetylamino)ethyl]thio]-6-ethyl-7-oxo-1-azabicyclo[3.2.0]hept-2-en-2-carboxylic acid, (4-nitrophenyl)methyl ester in 94% yields based on the starting cis-(±)-6-ethyl-3,7-dioxo-1-azabicyclo[3.2.0]heptan-2-carboxylic acid, (4-nitrophenyl)methyl ester.

M.p. 151° C.

I.R. (CDCl₃): 3430 (νNH), 1775 (νCO lactam), 1700 (νCO ester), 1670 and 1550 (amide I and II), 1610 (νCH arom.), 1525 and 1350 (νNO₂) cm⁻¹.

N.M.R. (CDCl₃, 270 MHz, δ): 1.04 (t, 3H, CH₃—CH₂—), 1.49–1.94 (2ddq, 2H, CH₃—C$\underline{H}$₂—), 2.0 (s, 3H, —NH—CO—CH₃), 2.86–3.64 (m, 7H,

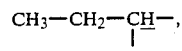

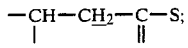

S—CH₂—CH₂—N), 4.32 (ddd, 1H, J$_{cis}$=5.5 Hz,

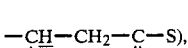

5.23–5.5 (dd, 2H, —C$\underline{H}$₂—φ), 6.01 (s, 1H, —N$\underline{H}$ COCH₃), 7.66 (d,2H,J$_{ortho}$=8.5 Hz,

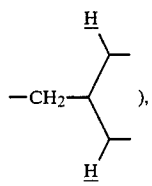

8.23 (d, 2H,

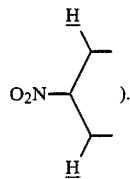

EXAMPLE 12

Thienamycin

The compound of the title is prepared by following the procedure schematically described in Charts I and III and illustrated in detail in the foregoing examples, starting from 1,3-hexadien-5-(4-nitrobenzyloxycarbonyloxy)-1-ol acetate wherein the carbon atom which bears the protected hydroxy group (C₅) has the same configuration as the 8-positioned carbon atom in the naturally occurring thienamycin.

In this particular case, where the introduction of a —S—CH₂—CH₂—NH₂ group is desired, also the amino group of the nucleophile R'''—SH has to be protected in order to avoid side reactions. It has been found that also in the case of the amino group, the nitrobenzyloxycarbonyl group is a particularly preferred protecting group. Deprotection of the amino group as well as of the C8-hydroxy group and the 2-ester group is then achieved by the usual methods.

We claim:

1. A β-lactam acetic acid derivative having the formula

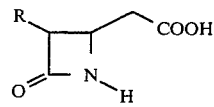

wherein R represents alkyl, mono-substituted alkyl substituted with amino, mono- and di-alkylamino wherein the alkyl group has from 1 to 6 carbon atoms or alkenyl wherein the alkenyl group has from 3 to 6 carbon atoms, and its carboxylic acid salts.

2. A compound as in claim 1 wherein R represents alkyl.

3. A compound as in claim 2 wherein R is ethyl.

4. A compound according to claim 1 wherein the hydrogen atoms at position 2 and 3 have trans stereochemistry.

* * * * *

UNITED STATES PATENT AND TRADEMARK OFFICE
CERTIFICATE OF CORRECTION

PATENT NO. : 4,576,746

DATED : March 18, 1986

INVENTOR(S) : Duccio Favara et al.

It is certified that error appears in the above-identified patent and that said Letters Patent is hereby corrected as shown below:

At column 13, line 6, the patent reads "into a 2 1" and should read --into a 2 · 1--

At column 28, lines 5-10 and again at column 28, lines 50-55, the patent reads

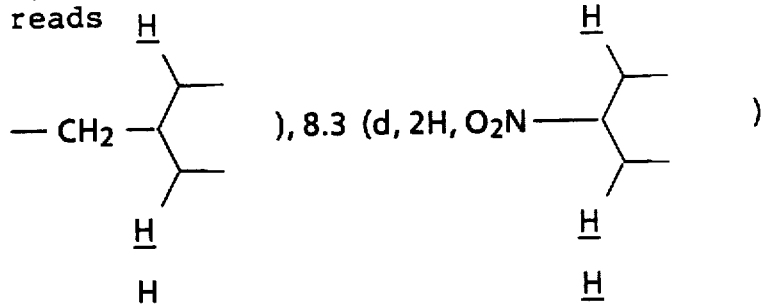

and should read

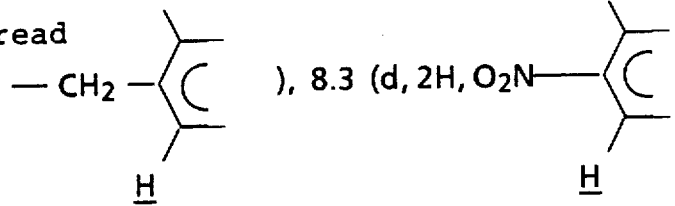

At column 29, lines 30-35 and again at column 30, line 35, the patent reads

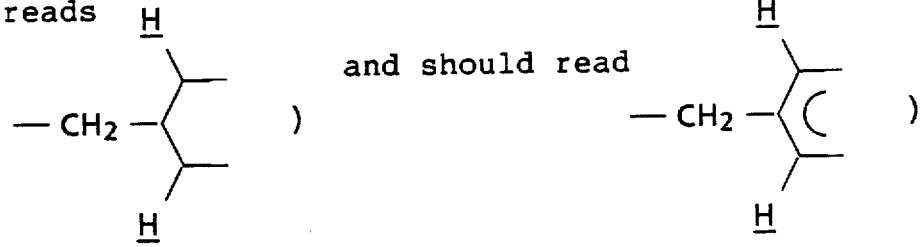 and should read 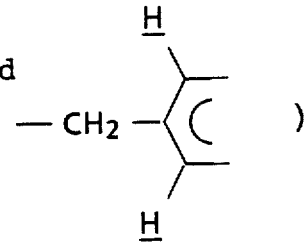

UNITED STATES PATENT AND TRADEMARK OFFICE
CERTIFICATE OF CORRECTION

PATENT NO. : 4,576,746

DATED : March 18, 1986

INVENTOR(S) : Duccio Favara et al.

It is certified that error appears in the above-identified patent and that said Letters Patent is hereby corrected as shown below:

At column 29, lines 40-45 and again at column 30, line 45, the patent reads 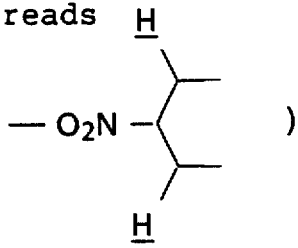 and should read 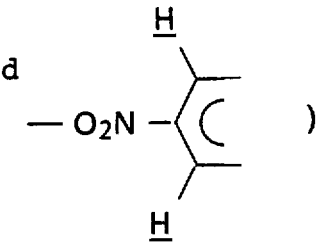

Signed and Sealed this

Fourth Day of December, 1990

Attest:

HARRY F. MANBECK, JR.

*Attesting Officer*   *Commissioner of Patents and Trademarks*